(12) United States Patent
Haber et al.

(10) Patent No.: US 6,248,933 B1
(45) Date of Patent: Jun. 19, 2001

(54) CELLULAR BASIS OF VASCULAR-GRAFT STENOSIS

(75) Inventors: Edgar Haber, deceased, late of Salisbury, NH (US), by Carol Haber, legal representative; Chengwei Shi, Short Hills, NJ (US); Nicholas E. S. Sibinga, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/188,081

(22) Filed: Nov. 6, 1998

Related U.S. Application Data
(60) Provisional application No. 60/064,919, filed on Nov. 7, 1997.

(51) Int. Cl.[7] ...................... A01K 67/027; A01K 67/033; A61K 49/00; A61K 35/34; A01N 1/00

(52) U.S. Cl. ..................................... 800/18; 800/3; 800/9; 800/13; 800/14; 800/18; 424/9.2; 424/569; 435/1.1; 435/320.1; 600/36

(58) Field of Search .................................. 800/9, 18, 2, 3, 800/8, 13, 21, 14; 514/44; 435/1.1, 1.2, 320.1; 424/422, 423, 9.2, 569; 600/36

(56) References Cited

U.S. PATENT DOCUMENTS 5,675,062 * 10/1997 Haber et al. ............................. 800/2

OTHER PUBLICATIONS

McCann et al. Artery. 6(4): 267–79, 1980.*
Feldman et al. Fundamentals of Clinical Pharmacology. 9: 8–16, 1995.*
Koveker et al. Surgery. 109: 313–9, Mar. 1991.*
Carmeliet et al. Journal of Clinical Investigation. 99(2): 200–208, Jan. 1997.*
Bryan et al. Current Opinion in Cardiology. 9(6): 641–9, Nov. 1994.*
Zwolak et al. Arteriosclerosis, 9(3): 374–9, May 1989.*
Faries et al. Journal of Vascular Surgery. 24(3): 463–471, 1986.*
Mullins et al. J Clin Investigation. 98(11): S37–40, Dec. 1996.*
Palmiter et al. Ann. Rev. Genet. 20: 465–99, May 1989.*
Moreadith et al. J Mol Med 75: 208–216, May 1989.*
Zou et al., "Mouse Model of Venous Bypass Graft Arteriosclerosis", *American Journal of Pathology*, 153:1301–1310, 1998.
Betsholtz, "Role of platelet–derived growth factors in mouse development", *The International Journal of Developmental Biology*, 39:817–825, 1995.
Carmeliet et al., "Gene Targeting and Gene Transfer Studies of the Biological Role of the Plasminogen/Plasmin System", *Thrombosis and Haemostasis*, 74:429–36, 1995.

Carmliet et al., "Impaired Arterial Neointima Formation in Mice with Disruption of the Plasminogen Gene", *The Journal of Clinical Investigation*, 99:200–208, 1997.
Cubitt et al., "Differential Induction of GROα Gene Expression in Human Corneal Epithelial Cells and Keratocytes Exposed to Proinflammatory Cytokines", *Investig. Ophthalmalogy & Visual Sci.*, 38:1149–1158, 1997.
Czubayko et al., "Ribozyme–targeting Elucidates a Direct Role of Pleiotrophin in Tumor Growth", *The Journal of Biological Chemistry*, 269:21358–21363, 1994.
Gao et al., "Impaired Host Defense, Hematopoiesis, Granulomatous Inflammation and Type 1–Type 2 Cytokine Balance in Mice Lacking CC Chemokine Receptor 1", *The Journal of Experimental Medicine*, 185:1959–1968, 1997.
Kobayashi et al., "Reversal of Drug Sensitivity in Multidrug–Resistant Tumor Cells by an MDR1 (PGY1) Ribozyme", *Cancer Research*, 54:1271–1275, 1994.
Nakamuta et al., "Complete Phenotypic Characterization of apobec–1 Knockout Mice with a Wild–type Genetic Background and a Human Apolipoprotein B Transgenic Background, and Restoration of Apolipoprotein B mRNA Editing by Somatic Gene Transfer of Apobec–1", *The Journal of Biological Chemistry*, 271:25981–25988, 1996.
Roder et al., "The beige mutation in the mouse selectively impairs natural killer cell function", *Nature*, 278:451–453, 1979.
Russell et al., "Early and persistent induction of monocyte chemoattractant protein 1 in rate cardiac allografts", *Proceedings of the National Academy of Sciences (USA)*, 90:6086–6090; 1993.
Russell et al., "Identification and Upregulation of Galactose/N–acetylgalactosamine Macrophage Lectin in Rat Cardiac Allografts with Arteriosclerosis", *The Journal of Clinical Investigation*, 94:722–730, 1994.
Schultz et al., "Genetically Determined Murine Models of Immunodeficiency", *Ann. Rev. Immunol.*, 5:367–403, 1987.
Stevenson et al., "Phenotypic Correction of Hypercholesterolemia in ApoE–Deficient Mice by Adenovirus–Mediated In Vivo Gene Transfer", *Arteriosclerosis, Thrombosis and Vascular Biology*, 15:479–484, 1995.
Sullivan, "Development of Ribozymes for Gene Therapy", *The Journal of Investigative Dermatology*, 103:85s–89s, 1994.

(List continued on next page.)

Primary Examiner—Deborah J. R. Clark
Assistant Examiner—Carrie Stroup
(74) Attorney, Agent, or Firm—Ingrid A. Beattie; Mintz, Levin, Cohn, Ferris, Glovsky and Popeo, P.C.

(57) ABSTRACT

A mouse model for vein graft stenosis useful for identifying compounds which reduce or prevent such stenosis, consisting of a mouse engrafted with an autogenous vein which exhibits detectable stenosis within 30 days of transplantation. Also disclosed are therapeutic methods for inhibiting the development of vein graft stenosis.

19 Claims, 1 Drawing Sheet

OTHER PUBLICATIONS

Wang et al., Human Recombinant Macrophage Inflammatory Protein–1α and–β and Monocyte Chemotactic and Activating Factor Utilize Common and Unique Receptors on Human Monocytes, *J. Immunol.*, 150:3022–3029, 1993.

Watanabe et al., "Mice deficient in cystathionine β–synthase: Animal models for mild and severe homocyst(e)inemia", Proceedings of the National Academy of Sciences (USA), 92:1585–1589, 1995.

Wiktor–Jedrzejczak et al., "Total absence of colony–stimulating factor 1 in the macrophage–deficient osteopetrotic (op/op) mouse", Proceedings of the National Academy of Sciences (USA), 8:4828–4832, 1990.

Xu et al., "Human Apolipoprotein E2, E3, and E4 Isoform–Specific Transgenic Mice: Human–Like Pattern of Glial and Neuronal Immunoreactivity in Central Nervous System Not Observed in Wild–Type Mice", *Neurobiology of Disease*, 3:229–245, 1996.

Yoshida et al., "The murine mutation osteopetrosis is in the coding region of the macrophage colony stimulating factor gene", *Nature*, 345:442–444, 1990.

\* cited by examiner

US 6,248,933 B1

CELLULAR BASIS OF VASCULAR-GRAFT STENOSIS

This application claims priority from Provisional application Ser. No. 60/064,919, filed on Nov. 7, 1997.

BACKGROUND OF THE INVENTION

This invention relates to vascular graft stenosis. About 400,000 patients undergo aorta-coronary artery bypass graft surgery annually in the United States. Unfortunately, the grafts often require subsequent intervention because of the development of hemodynamically significant lesions on the lumenal side of the intima, which is the innermost layer of the artery. The occlusion in the artery resulting from the lesion is known as a stenosis. Within two years of the surgery, up to 30% of vein grafts develop stenosis. Ten years after surgery, stenosis has occurred in approximately 50% of vein grafts.

The factors involved in causing graft stenosis are largely unknown, and there is a lack of an adequate animal model for characterizing graft stenosis.

SUMMARY OF THE INVENTION

The invention features a rodent model, e.g., a mouse model, of vascular graft stenosis in which the stenosis develops rapidly and closely mimics the development of vascular graft stenosis in humans.

The invention provides a surgically modified mouse in which a blood vessel, e.g, an artery or vein, has been transplanted into, i.e., spliced into, an endogenous artery. Preferably, a segment of a histocompatible, e.g., autogenous, vessel is used. Graft stenosis is detected within 30 days, preferably within 20 days, more preferably within 10 days, and most preferably within 7 days of transplantation. The transplanted vessel is preferably 10% occluded, more preferably 25% occluded, even more preferably 50% occluded, and most preferably 75–100% occluded.

By "autogenous" is meant that the donor vessel is obtained from the recipient animal.

The donor blood vessel can be any vein or artery, e.g., the jugular or saphenous, vein. The endogenous artery (i.e., the tissue serving as the recipient of the grafted tissue) can be any suitable artery, e.g., the carotid, femoral or aortic artery. Preferably, the transplanted artery is the carotid artery.

The mouse of the invention may be made using mouse strains harboring one or more mutations, e.g., gene deletions, e.g., in genes encoding platelet derived growth factor (PDGF) or plasminogen; OP/OP homozygous mice (a spontaneous mutant strain in which macrophage colony stimulation factor (MCSF) is absent with consequent marked reduction in macrophage production); Beige (Bg) mice (a spontaneous mutant strain in which natural killer cell function is deficient); or mice lacking the CC chemokine receptor 1 gene, the cystathione beta-synthase (CBS) gene, or the apoE gene.

The invention also provides an in vivo screening assay to determine whether a compound reduces vein graft stenosis. The method involves the steps of providing a first and second mouse, each of which contains a histocompatible autogenously transplanted vein; contacting the first mouse with a candidate compound and the second mouse with a vehicle alone; and comparing the degree of vein graft stenosis in the grafts of each mouse within 20 days after transplantation. Alternatively, the second mouse may simply be maintained in the absence of the candidate compound. The candidate compound is preferably a compound which inhibits vascular smooth muscle cell proliferation or inflammation, e.g., macrophage activity, either directly or indirectly. Evidence of vein graft stenosis can be detected in the vein grafts as early as 7 days after transplantation. The vein grafts may be removed from the mice at any point during the assay and preserved, e.g., frozen for subsequent analysis. The candidate compound or vehicle may be administered locally to each mouse so as to contact the vein graft directly; alternatively, the compound or vehicle may be delivered systemically so the vein graft is contacted with compound via the circulatory system. A lesser degree of stenosis in the graft of the first mouse compared to the graft of the second mouse is an indication that the candidate compound reduces vein graft stenosis. In the absence of contact with the candidate compound, vein graft stenosis in the second mouse is at least 100% greater, more preferably at least 150% greater, and most preferably 300% greater, than that of the first mouse.

Also included in the invention is an in vivo screening assay to determine whether a gene encodes a gene product that increases or decreases vein graft stenosis. The method includes the steps of providing a first mouse and second mouse: the first mouse has a mutation in a gene to be tested and the second mouse has at least one functional copy of the gene. The first mouse further includes a vein autogenously transplanted into an artery of the first mouse, and the second mouse further includes a second vein autogenously transplanted into an artery of the second mouse. The degree of vein graft stenosis in the transplanted veins in the first mouse is compared to that of the second mouse. An increase or decrease in vein graft stenosis in the first mouse compared to said second mouse indicates that the gene product increases or decreases, respectively, vein graft stenosis.

Compounds that inhibit the expression or function of genes or gene products that increase vein graft stenosis are administered to patients to prevent or decrease the development of stenosis associated with vascular injury, e.g., vein graft stenosis.

Degree of vein graft stenosis may be determined by physically measuring neointimal thickening, or by characterizing and enumerating cells involved in the rejection process, e.g., smooth muscle cells, leukocytes, macrophages, and subpopulations of lymphocytes ($CD4^+$ and $CD8^+$ cells). The intima is defined as the region between the lumen and the internal elastic lamina of the artery; the media is defined as the region between the internal and external elastic laminae; and the adventitia is defined as the region outside the external elastic lamina of the artery. Functional activity, e.g., production of cytokines, of the infiltrating cells can also be measured to determine the degree of graft stenosis. Replicating cells which contribute to the formation of the graft stenosis may be detected by expression of proliferating cell nuclear antigen (PCNA).

The invention also includes a method of making the surgically modified mouse. The method can be carried out as follows: a mouse is provided; a blood vessel, preferably a vein, which is not part of a solid organ, or which has been removed from a solid organ ("the transplant vessel") is surgically removed from the mouse, and the vessel is surgically attached (spliced) to an endogenous artery of either the first mouse or a second mouse, such that the functional integrity of the blood vessel is restored, i.e., pulsation of the vessel and blood flow through the artery is evident.

The invention also includes a method of inhibiting vein graft stenosis in a recipient mammal by administering to the recipient a compound which inhibits vascular smooth muscle cell proliferation, or by administering to the recipient a compound which inhibits macrophage activity. Alternatively, the method may be carried out by contacting a donor blood vessel or organ either in vivo or ex vivo with a compound which inhibits macrophage activity, and if the contacting step was carried out ex vivo, then transplanting the organ into the recipient mammal. Preferably, the compound inhibits expression or activity of macrophage colony stimulating factor or galactose/N-acetylgalactosamine macrophage lectin. The compound may also inhibit expression of the oligosaccharide, galactose/N-acetylgalactosamine (which binds to galactose/N-acetylgalactosamine macrophage lectin), in the donor blood vessel or organ. Antibodies which bind to either the macrophage lectin or its oligosaccharide ligand may be used to block binding of lectin to its oligosaccharide ligand, thereby inhibiting macrophage activity at the graft site. The compound may inhibit macrophage colonization of the donor organ or blood vessel, for example, by inhibiting expression or activity of a macrophage or monocyte chemoattractant protein. An antibody which binds to a macrophage or monocyte chemoattractant protein may also be used to inhibit macrophage colonization of the engrafted organ. For example, antibodies which bind to chemoattractant factors such as monocyte chemoattractant protein-1, macrophage inflammatory protein-1α, or macrophage inflammatory protein-1β, may be administered to the recipient to inhibit macrophage migration to the graft site.

The invention offers many advantages. The development of vein graft stenosis in the inventive model closely parallels the development of the condition in humans. Like the human disease, staged development of lesions with mixed cellular characteristics involving both inflammatory cell and smooth muscle cell accumulation occurs in the mouse of the invention. Both diffuse and concentric intimal hyperplasia develops in the model, and the model can be used for determining the roles in human vein-graft stenosis of genes involved in many components of smooth muscle cell proliferation or an inflammatory response. The model results in a consistent and reproducible neointima composed mainly of smooth muscle cells, thereby mimicking human vein-graft stenosis and restenosis. This model is useful for identifying therapeutic agents for treating vein graft associated restenosis, and in developing therapeutic interventions for these conditions.

A second advantage is the accelerated pace at which lesions associated with vein graft stenosis develop. A neointima begins to develop in allografts as early as 7 days after grafting, and it becomes a nearly occlusive lesion after 20 days. The pace of development of graft stenosis in the mouse of the invention allows the evaluation of drugs or other types of therapeutic intervention in 20 days or less.

Another advantage of the invention is that the graft procedure can be carried out subcutaneously at an accessible location, e.g., in the neck, and is not technically complex. As a result, transplantation success rate is relatively high in the mice of the invention with carotid artery grafts. Because the common carotid artery is unbranched from its origin in the aorta to its bifurcation, quantitation and morphometric studies are simplified.

Other features and advantages of the invention will be apparent from the following description of the invention and from the claims.

DETAILED DESCRIPTION

Figure 1:
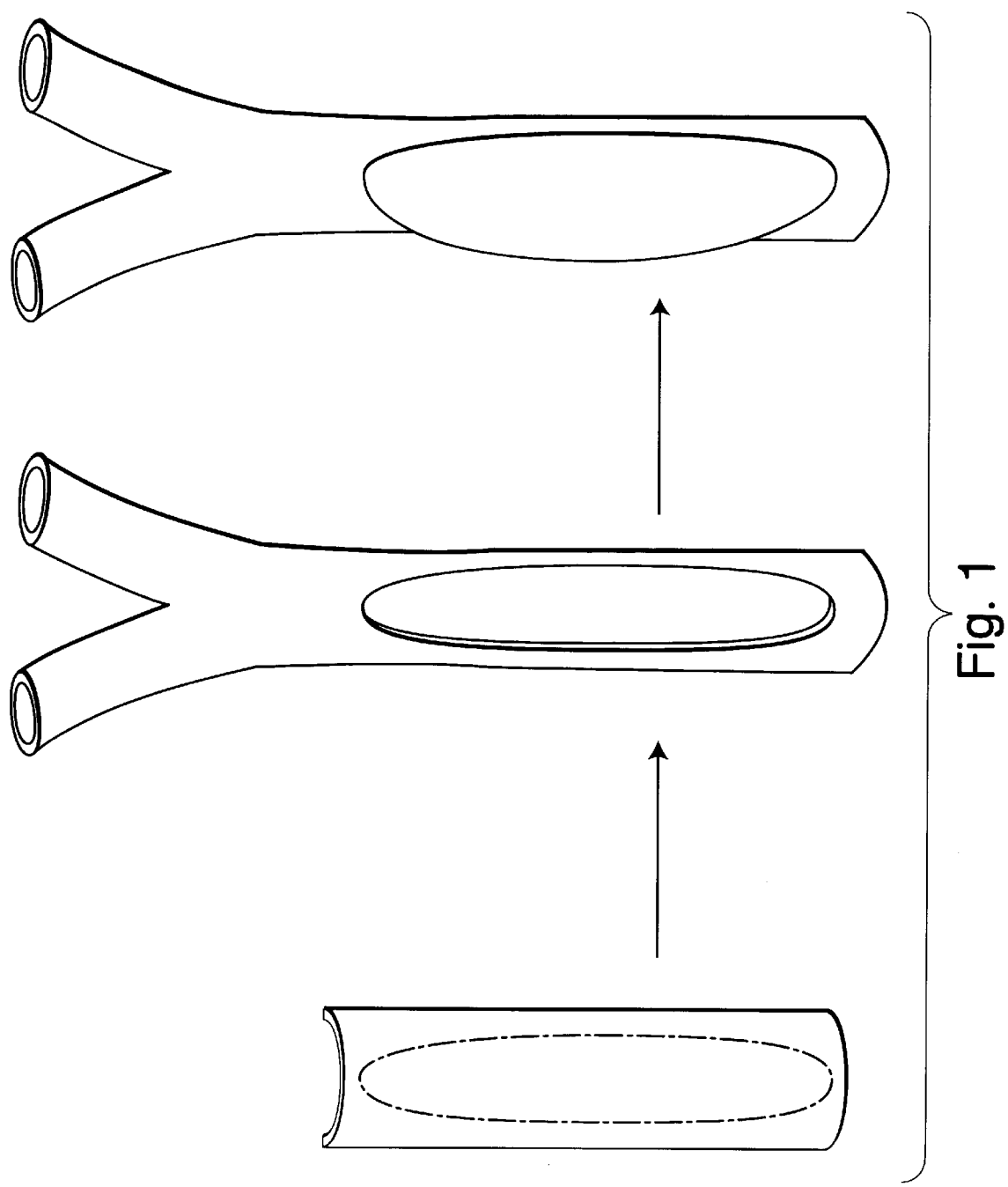
FIG. 1 is a diagram of a vein grafted into a carotid artery.

The invention provides an accelerated model for vein graft stenosis. The mouse of the invention reproduces many of the features of human vein graft stenosis at an accelerated pace and can be used to test a variety of therapeutic interventions for the prevention or treatment of vein graft stenosis. The mouse can also be used to determine the roles of genes that encode components involved in the development of graft stenosis.

In many respects, the morphologic features of this mouse vascular transplant model resemble those of human vein graft stenosis. The arterial lesions in the mouse of the invention are characterized by diffuse and concentric intimal proliferation, with a dominance of smooth muscle cells.

Identification of Compounds Capable of Reducing or Inhibiting Vein Graft Stenosis The mouse of the invention and the methods of the invention can be used to screen compounds or other therapeutic approaches for the ability to inhibit the development of stenosis in vein grafts. In such an assay, mice into which a vessel, preferably an autogenous vein, has been transplanted are treated, e.g., contacted with a candidate compound, or left untreated, i.e., no compound whatsoever is administered, or a vehicle alone is administered. As an internal control, a second vein may be engrafted into the recipient mouse or into a second mouse of the same strain as a control. The second graft is left untreated or contacted with vehicle alone.

The transplanted arteries of treated and untreated animals (or the treated and untreated arteries with the same animal) are then evaluated at various time points for the development of stenosis, as described below. A reduction of neointimal thickening or other indication of vein graft stenosis, e.g., infiltration of inflammatory cells or detection of actively proliferating cells, in the grafted arteries of treated mice compared to those of the untreated mice indicates that the candidate compound is efficacious in the treatment and/or prevention of vein graft stenosis.

Methods of Evaluating Vein Graft Stenosis

Specimens of the transplanted arterial tissue can be prepared using standard histological methodology. For example, tissues can be set into paraffin or frozen prior to cutting into thin sections for microscopic evaluation.

Development of vein graft stenosis, i.e., formation of a neointima, can be measured using methods well known in the art, e.g., immunohistochemical, histological, and morphometric techniques as described in U.S. Pat. No. 5,675,062. Cellular responses involved in the graft rejection process can be identified by characterizing cell types, e.g., smooth muscle cells, leukocytes, macrophages, and subpopulations of T cells, e.g., $CD4^+$ T cells and $CD8^+$ T cells present in the neointima. The state of activation of cells in the neointima can also be evaluated by detecting PCNA, a marker of cell replication. The size, i.e., the area, of the neointima can also be measured.

Animals

The invention permits exploitation of the genetic resources of commercially available murine strains. Genetics of the mouse have been extensively characterized. As a result, a large number of mouse strains and murine cell lines that manifest specific gene mutations and deletions are available. The mouse of the invention and the assays of the invention may utilize mouse strains that have been subjected to targeted gene deletions. Thus, the mouse of the invention makes possible the elucidation of the detailed pathogenesis of vein graft stenosis and the definition of events and/or molecules that may serve as targets for therapeutic intervention.

Mouse strains in which genes central to vascular smooth muscle cell proliferation or to initiating and maintaining an inflammatory response have been inactivated, are readily available. Such mouse strains can be used according to the invention to define the specific roles of those genes to the pathogenesis of the disease. Mice that have deficient macrophage function (Yoshida et al., Nature, 1990, 345:442–444), or those that lack B lymphocytes (nu) (Shultz et al., Ann. Rev. Immunol., 1987, 5:367–403) or natural killer cells (bg) (Shultz et al. supra) can be used to evaluate the cellular contribution to the development of vein graft stenosis. Any strain of mice can be used as the donor and recipient in the inventive model. The mice can have mutations, e.g., knockout mutations, in genes involved in vascular smooth muscle cell proliferation, e.g., PDGF-1 (Betsholtz, Int. J. Dev. Biol. 39:817, (1995)), plasminogen (Carmeliet et al., J. Clin. Invest. 99:200, (1997)). The mice can also have mutations in genes involved in mediating inflammatory responses, e.g., the OP/OP mouse, which encodes macrophage colony stimulating factor and which has a phenotype characterized by reduced numbers of macrophages (Wiktor-Jedrzejcak et al., PNAS 87:4828 (1990)); mice lacking the CC chemokine receptor 1 (Gao et al., J. Exp. Med. 185:1959 (1997), or the Biege homozygote, a recessive mutation on chromosome 13 that has reduced numbers of natural killer cells (Roder et al., Nature 278:451 (1979)). The mice may alternatively have mutations in genes associated with altered levels of stenosis or arteriosclerosis, e.g., the apoE gene (Stevenson et al., Arterioscler. Thromb. Vasc. Biol. 15:479 (1995)) and the cystathione beta-synthase (CBS) gene (Watanabe et al., Proc. Nat. Acad. Sci. (USA) 92:1585 (1995)).

Each of the mouse strains can be tested for deletion of the cell type in question either by fluorescence-activated cell sorting of peripheral blood or by immunohistochemical examination of the spleen.

The invention will be further described in the following examples, which do not limit the scope of the invention described in the claims.

EXAMPLE 1
Development of Vein Graft Stenosis in a Mouse Model

Vein-graft stenosis was generated in C57BL/6 mice by engrafting a segment of autogenous jugular vein into a defect in the carotid artery (produced by cutting out a piece of the vessel wall) as shown in FIG. 1. The time course of lesion development was characterized and major cell types were identified by immunohistochemical staining.

Within 7 days, the vein-patch graft formed a neointima 2 to 5 cell layers thick. Neointimal cell accumulation was detected predominantly on the side of the artery adjoining the venous tissue graft. Most of the cells stained positive for α-actin, a marker for smooth muscle cells. CD45-positive mononuclear leukocytes were also present in small numbers in the neointima and quite abundantly in the adventitia. Mural thrombi (fibrin deposits) were also formed at this stage (within days after engraftment) and disappeared by day 20. At day 20, the neointima became exuberant and resulted in 65.57±13.25% luminal occlusion. Smooth muscle cells, the dominant cell type in the neointima, accounted for 42.92±4.92% of the total area, whereas collagen deposition (indicative of smooth cell proliferation) accounted for 20.2±1.42% of total area. CD45-positive leukocytes only accounted for 4.5±1.46% of the intimal cellular components. Cells staining for PCNA were also present in the intima (15.17±5.9%) by 20 days, indicating the proliferation of mononuclear leukocytes and smooth muscle cells.

In addition to its use as a screening tool, the mouse of the invention also provides a powerful tool for dissecting the relative contributions that vascular smooth muscle cell proliferation, collagen deposition, humoral antibodies, specific cytokines or growth factors, cytotoxic T cells, and macrophages make to the pathogenesis of vein graft stenosis.

EXAMPLE 2
Treatment of Vein Graft Stenosis

Therapeutic approaches, such as gene therapy, antisense therapy, ribozyme therapy, and antibody therapy are used to inhibit the mechanisms involved in the development of neointimal thickening.

Antisense therapy is used to inhibit expression of proteins involved in the development of vein graft stenosis. The antisense strand (either RNA or DNA) is directly introduced into the cells in a form that is capable of binding to the mRNA transcripts. Alternatively, a vector-containing sequence which, which once within the target cells is transcribed into the appropriate antisense mRNA, may be administered. Antisense nucleic acids which hybridize to mRNA can decrease or inhibit production of the polypeptide product encoded by a gene by associating with the normally single-stranded mRNA transcript, thereby interfering with translation and thus, expression of the protein.

Ribozyme therapy can also be used to inhibit gene expression. Ribozymes bind to specific mRNA and then cut it at a predetermined cleavage point, thereby destroying the transcript. These RNA molecules may be used to inhibit expression of a gene encoding a protein involved in the formation of vein graft stenosis according to methods known in the art (Sullivan et al., 1994, J. Invest. Derm. 103:85S–89S; Czubayko et al., 1994, J. Biol. Chem. 269:21358–21363; Mahieu et al, 1994, Blood 84:3758–65; Kobayashi et al. 1994, Cancer Res. 54:1271–1275).

Another therapeutic approach to inhibiting the expression of proteins or polypeptides involved in the development of vein graft stenosis is the production of intracellularly expressed antibodies which, when expressed in a cell, bind to and prevent the transport and surface expression of target proteins. Intracellular antibodies may be expressed in a cell using known techniques (Chen et al., 1994, Hum. Gene Ther. 5:595–601) to inhibit cell surface proteins such as MHC Class II antigens or secreted proteins such as immunoglobulins.

A nucleic acid may be introduced into cells of a donor blood vessel or directly into the mammalian recipient by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

A therapeutic composition may include one or more compounds, e.g., nucleic acids or immunosuppressive agents, and a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result in a treated animal, e.g., inhibition of expression of a target gene, e.g., a cell surface or secreted protein, or inhibition of cell activity, e.g., proliferation, migration, antigen presentation, antibody production, or cytokine production.

Parenteral administration, such as intravenous, subcutaneous, intramuscular, and intraperitoneal delivery routes, may be used to deliver the compound, with intravenous administration being the preferred route. Dosages for any one patient depends upon many factors, including the patient's size, body surface area, age, the particular compound to be administered, sex, time and route of administration, general health, and other drugs being administered concurrently. Dosages of the compound to be administered will vary (doses of immunosuppressive agents are expected to be in the range of doses used for administration of other immunosuppressive agents known in the art). A preferred dosage for intravenous administration of nucleic acids is from approximately $10^6$ to $10^{22}$ copies of the nucleic acid molecule. Alternatively, the compound may be administered via a timed-release implant placed in close proximity to the engrafted organ.

Ex vivo treatment of the donor blood vessel may be carried out by immersing the blood vessel in a solution containing a compound or therapeutic composition, e.g., a nucleic acid (e.g., antisense sequence, coding sequence, or ribozyme) prior to transplantation. Alternatively, an organ may be perfused or electroporated with solution containing a therapeutic composition.

EXAMPLE 3
Macrophages as a Therapeutic Target

Macrophages migrate to the site of the engrafted tissue, colonize the graft, and participate in the development of vein graft stenosis. Therapeutic approaches can therefore be taken to inhibit the migration of macrophages to the graft site as well as to inhibit the activity of macrophages at the graft site. Antibodies specific for macrophage or monocyte chemoattractant proteins or migration proteins may be administered to the donor organ or blood vessel directly (ex vivo) or to the recipient mammal (in vivo) to inhibit macrophage migration to and colonization of the engrafted organ. The expression of macrophage proteins, e.g., galactose/N-acetyl galactosamine macrophage lectin (Russell et al., 1994 J. Clin. Invest. 94:722–730), monocyte chemoattractant protein-1 (Russell et al., 1993, Proc. Natl. Acad. Sci. U.S.A., 90:6086–6090; Brieland et al. 1993, Am. J. Respir. Cell. Mol. Biol. 98:300–305), macrophage inflammatory-1α, or macrophage chemoattractant protein-1β (Wang et al., 1993, J. Immunol. 150:3022–3029), may be inhibited using antisense therapy, ribozyme therapy, or intracellular antibody therapy. Expression of the galactose/N-acetyl galactosamine macrophage lectin ligand, galactose/N-acetyl galactosamine oligosaccharide, in the donor organ or blood vessel may also be inhibited using the gene therapy techniques described above. Antibodies to these proteins may be administered ex vivo or in vivo to inhibit receptor-ligand binding and therefore the activation of macrophage function, e.g., secretion of cytokines which stimulate smooth muscle cell proliferation, at the graft site. Other potential inhibitors of macrophage activity may be tested for the ability to inhibit vein graft stenosis using the screening assays of the invention. Such compounds may be administered as described above.

EXAMPLE 4
Comparison of Vein Graft Stenoses in Wild-type Mice and Mice Lacking a Functional Plasminogen Gene Arterial neointimal formation due to electrostatic and immune-mediated injury is impaired in mice lacking a functional plasminogen gene. To determine if plasminogen is also required for responding to venous injury, vein grafts were compared in wild-type mice and in mice lacking a functional plasminogen gene.

A patch cut from the external jugular vein of a mouse expressing a wild-type plasminogen gene (wild type mice) was used a graft to repair a surgically-created defect in the carotid artery of the same mouse. Analogous grafting was also performed on mice in which plasminogen genes had been deleted (plasminogen knockout mice; Carmeliet et al., 1997, J. Clin. Invest. 99:200). The grafts in the two mice populations were then characterized morphologically and histologically.

In wild-type mice, the arteriovenous graft showed initial endothelial denudation, modest mural thrombosis, and formation of a neointima that progressively and reproducibly expanded in a manner analogous to human vein graft disease, but at an accelerated pace. At day 7, the neointima occupied 37±4.6% of the vessel lumen and contained equal areas of CD45-positive leukocytes and α-actin-positive smooth muscle cells. At day 20, the neointima increased to 66±5.7% of the lumen, and smooth muscle cells were dominant. The proliferative index of neointimal cells assessed by PCNA staining was 50.6±3.6% at day 7 and 15.2±2.0% at day 20. α-actin positive staining smooth muscle cells accounted for 9.9±1.1% of intimal area at day 7 and 40.9±2.6% at day 20. Cells staining positive for collagen accounted for 6.8±0.7% of intimal area at day 7 and 20.7±1.8% at day 20.

In mice lacking a functional plasminogen gene vein graft neointimal formation was not significantly different from that in control animals (70.9±6.4 vs. 65.6±4.4% lumenal occlusion, p=NS). Thus, plasmin, which appears to be critical for extracellular matrix degradation and cellular migration after arterial injury, does not substantially affect the degree of neointimal formation. This can be attributed to the relative lack of structural barriers to cellular migration in the normal vein wall. These results demonstrate that the model of vein graft injury is useful to identify genes or gene products that contribute to the development of vascular graft stenosis.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A mouse model for vein graft stenosis, said model comprising a recipient mouse comprising a vein patch surgically transplanted from a histocompatible donor mouse into a defect in an artery of said recipient mouse, wherein graft stenosis occurs within 30 days of transplantation.

2. The model of claim 1, wherein said vein patch is autologous.

3. The model of claim 1, wherein said vein patch is derived from a jugular vein.

4. The model of claim 1, wherein said artery is a carotid artery.

5. The model of claim 1, wherein said mouse is of the C57BL/6J strain.

6. The model of claim 1, wherein said recipient mouse has a knockout mutation in the gene encoding plasminogen.

7. An in vivo screening assay to determine whether a compound reduces vein graft stenosis, comprising:
  (a) providing a first mouse comprising a first vein patch autogenously transplanted into an artery of said mouse;
  (b) providing a second mouse histocompatible with said first mouse, said second mouse comprising a second vein patch autogenously transplanted into an artery of said second mouse;

(c) contacting said artery of said first mouse with a candidate compound either before or after autogenous transplantation of said first vein patch; and (d) comparing (1) the degree of vein graft stenosis in said artery of said first mouse which occurs within 30 days after transplantation of said artery, with (2) the degree of vein graft stenosis in said artery of said second mouse which occurs within 30 days after transplantation of said second artery, wherein a lesser degree of vein graft stenosis in said first artery compared to said second artery is an indication that said candidate compound reduces vein graft stenosis.

8. The screening assay of claim 7, wherein said candidate compound is an inhibitor of macrophage activity.

9. The screening assay of claim 7, wherein said candidate compound is an inhibitor of CD4-positive T cell activity.

10. The screening assay of claim 7, wherein said candidate compound is an inhibitor of B cell activity.

11. The screening assay of claim 7, wherein said candidate compound inhibits vascular smooth muscle cell proliferation.

12. The screening assay of claim 7, wherein said vein is a jugular vein and said artery is a carotid artery.

13. An in vivo screening assay to determine whether a plasminogen gene encodes a gene product that decreases vein graft stenosis, comprising:

(a) providing a first mouse and a second mouse, wherein said first mouse lacks a functional copy of said gene and said second mouse comprises at least one functional copy of said gene, said first mouse further comprising a vein patch autogenously transplanted into an artery of said first mouse and said second mouse further comprising a second vein patch autogenously transplanted into an artery of said second mouse;

(b) comparing the degree of vein graft stenosis in the transplanted artery in said first mouse and second mouse, wherein an increase in vein graft stenosis in said first mouse compared to said second mouse indicates that the gene product decreases vein graft stenosis.

14. An in vivo screening assay to determine whether a plasminogen gene encodes a gene product that increases vein graft stenosis, comprising:

(a) providing a first mouse and a second mouse, wherein said first mouse lacks a functional copy of said gene and said second mouse comprises at least one functional copy of said gene, said first mouse further comprising a vein patch autogenously transplanted into an artery of said first mouse and said second mouse further comprising a second vein patch autogenously transplanted into an artery of said second mouse;

(b) comparing the degree of vein graft stenosis in the transplanted artery in said first mouse and second mouse, wherein an increase in vein graft stenosis in said first mouse compared to said second mouse indicates that the gene product decreases vein graft stenosis.

15. An in vivo screening assay to determine whether a compound reduces vein graft stenosis, comprising:

(a) providing a first mouse comprising a first vein patch autogenously transplanted into an artery of said mouse;

(b) providing a second mouse histocompatible with said first mouse, said second mouse comprising a second vein patch autogenously transplanted into an artery of said second mouse;

(c) contacting said artery of said first mouse with a candidate compound either before or after autogenous transplantation of said first vein patch; and (d) comparing (1) the degree of vein graft stenosis in said first artery of said mouse which occurs within 30 days after transplantation of said artery, with (2) the degree of vein graft stenosis in said second artery of said second mouse which occurs within 30 days after transplantation of said second artery, wherein a lesser degree of vein graft stenosis in said first artery compared to said second artery is an indication that said candidate compound reduces vein graft stenosis.

16. A method of making a mouse comprising a vein graft stenosis, said method comprising (a) providing a recipient mouse; and (b) engrafting a vein patch from a histocompatible donor mouse into an artery of said recipient mouse, wherein graft stenosis occurs within 30 days of transplantation.

17. The method of claim 16, wherein said vein patch is derived from a jugular vein and said artery is a carotid artery.

18. The method claim 16, wherein said artery is a carotid artery.

19. The method of claim 16, wherein said vein patch is derived from a jugular vein.

* * * * *

UNITED STATES PATENT AND TRADEMARK OFFICE
CERTIFICATE OF CORRECTION

PATENT NO. : 6,248,933 B1
APPLICATION NO. : 09/188081
DATED : June 19, 2001
INVENTOR(S) : Edgar Haber et al.

Page 1 of 1

It is certified that error appears in the above-identified patent and that said Letters Patent is hereby corrected as shown below:

Please insert the following paragraph at column 1, line 2, after the title:

--STATEMENT AS TO FEDERALLY SPONSORED RESEARCH

This invention was made with government support under HL003274 awarded by the National Institutes of Health. The United States Government has certain rights in the invention.--

Signed and Sealed this

Seventh Day of September, 2010

David J. Kappos
*Director of the United States Patent and Trademark Office*